United States Patent
Albuschies

(10) Patent No.: US 9,366,643 B2
(45) Date of Patent: Jun. 14, 2016

(54) METHOD FOR PRODUCING AND ALIGNING NANOWIRES AND APPLICATIONS OF SUCH A METHOD

(76) Inventor: Joerg Albuschies, Zurich (CH)

( * ) Notice: Subject to any disclaimer, the term of this patent is extended or adjusted under 35 U.S.C. 154(b) by 203 days.

(21) Appl. No.: 14/240,265

(22) PCT Filed: Aug. 20, 2012

(86) PCT No.: PCT/EP2012/003530
§ 371 (c)(1),
(2), (4) Date: Jun. 16, 2014

(87) PCT Pub. No.: WO2013/026561
PCT Pub. Date: Feb. 28, 2013

(65) Prior Publication Data
US 2014/0285224 A1    Sep. 25, 2014

(30) Foreign Application Priority Data

Aug. 22, 2011  (EP) .................................... 11006842

(51) Int. Cl.
*G01N 27/04* (2006.01)
*G01N 33/483* (2006.01)
(Continued)

(52) U.S. Cl.
CPC ................. *G01N 27/04* (2013.01); *B82Y 40/00* (2013.01); *C30B 11/12* (2013.01); *C30B 29/06* (2013.01);
(Continued)

(58) Field of Classification Search
CPC .... C30B 29/605; C30B 11/00; C30B 25/005; G01N 33/54373; G01N 2610/00
USPC .................................................. 324/691, 71.1
See application file for complete search history.

(56) References Cited

U.S. PATENT DOCUMENTS

2005/0181587 A1    8/2005  Duan et al.
2006/0175601 A1*   8/2006  Lieber .................... B82Y 10/00
                                                          257/19
2008/0224122 A1    9/2008  Saitoh et al.

FOREIGN PATENT DOCUMENTS

WO         2007/136755 A2    11/2007

OTHER PUBLICATIONS

Chang et al., The fabrication of ZnO nanowire field-effect transistors by roll-transfer printing, Nanotechnology, 2009, pp. 1-6, vol. 20, No. 9, IOP Science, Great Britain.
(Continued)

*Primary Examiner* — Vincent Q Nguyen
(74) *Attorney, Agent, or Firm* — The Webb Law Firm

(57) ABSTRACT

In a method for producing a sensor element, a silicon nanowire having a diameter less than 50 nm is contacted via at least two points by electrodes. The nanowire and the electrodes are arranged on one plane on a substrate. Catalytically active metal nanoparticles having a diameter in the range of 0.5-50 nm are deposited on the surface of an insulating substrate and the surface and the metal nanoparticles deposited thereon are exposed to a gas flow containing a gaseous silicon component at a temperature in the range of 300-1100° C., whereupon, during a time period in the range of 10-200 minutes, a nanowire of a length in the range of 5-200 μm projecting from the substrate is formed. The nanowire projecting from the surface of the substrate is deposited in one plane with one of the contact surfaces corresponding to the surface of the insulating substrate by applying a secondary substrate, and either the nanowire deposited on the insulating substrate is contacted at two different points by electrodes or the nanowire adhering to the secondary substrate is contacted at two different points by electrodes.

29 Claims, 7 Drawing Sheets

(51) Int. Cl.
  *B82Y 40/00*  (2011.01)
  *C30B 11/12*  (2006.01)
  *C30B 29/06*  (2006.01)
  *C30B 29/60*  (2006.01)
  *G01N 33/487*  (2006.01)
  *B82Y 30/00*  (2011.01)

(52) U.S. Cl.
  CPC .............. *C30B 29/60* (2013.01); *G01N 33/483* (2013.01); *G01N 33/48721* (2013.01); *B82Y 30/00* (2013.01)

(56) References Cited

OTHER PUBLICATIONS

Fan et al., Wafer-Scale Assembly of Highly Ordered Semiconductor Nanowire Arrays by Contact Printing, Nano Letters, 2008, pp. 20-25, vol. 8, No. 1, Berkeley, California.

Albuschies et al., High-density silicon nanowire growth from self-assembled Au nanoparticles, Microelectronic Engineering, Feb. 20, 2006, pp. 1530-1533, vol. 83, Elsevier, Germany.

\* cited by examiner a)

b)

c)

d1)

d2)

METHOD FOR PRODUCING AND ALIGNING NANOWIRES AND APPLICATIONS OF SUCH A METHOD

TECHNICAL FIELD

The present invention relates to processes for producing and aligning nanowires and to applications of such a process; the present invention additionally relates to processes for producing nanofunnels in a single-crystal silicon substrate, and especially to uses of these processes or of the structures resulting therefrom for production of a molecular sensor having high sensitivity and processes for operation thereof.

STATE OF THE ART

For the formation of electrical contacts to nanowires on an insulating substrate in a lateral manner, it is necessary to align the nanowires in parallel to the substrate. The difficulty therein is to obtain nanowires parallel to the insulating substrate. For this step, two approaches are currently being pursued:
a) Directed lateral growth, such that there is no need for subsequent alignment. This is very difficult to achieve, since insulating substrates are amorphous and nanowires cannot define any direction of crystalline growth.
b) The nanowires can be detached from a growth substrate and (usually suspended in liquid) transferred to another substrate and deposited thereon laterally on the insulating substrate (electrophoresis/microfluidics/contact printing . . . ). Problem: localization and orientation of the nanowires is difficult to achieve, particularly with regard to the industrial parallel manufacture of several components at the wafer level. Particularly in relation to the formation of contacts with individual/few nanowires between defined metal electrodes, there is currently no economically viable method that can be parallelized.

SUMMARY OF THE INVENTION

By means of (rough) optical lithography in the micrometer range (>1 µm) and a very rough lateral direction tolerance for optical lithography (>1 µm), individual nanowires of micrometer length can form electronic contacts laterally on an insulating substrate. For this operation, the nanowires are produced (grown) on micrometer-size, locally defined, round nucleation areas on the final substrate, without having to transfer them from one substrate to another for the operation. In this case, the nanowires have a random orientation in relation to the substrate surface (3D). A novel alignment operation allows alignment of the random orientation of the nanowires (which are anchored to the substrate at one end) parallel to the substrate (2D), while they are still anchored to the substrate at one end. The nanowires can be aligned radially from their growth site outward toward the substrate. This enables the formation of electrical contacts to individual nanowires—lying laterally on the substrate—with conductive metal electrodes by means of optical lithography. The nanowires are contact-connected to a circular electrode over the center of the nucleation area. The second electrode is in an annular arrangement outside the first electrode and forms contacts with the ends of the nanowires directed outward. For transistor applications, a gate electrode can likewise be mounted between the two circular and annular electrodes via the nanowires, in order to produce nanowire transistors. Although there are preferred shapes, for example, with the circular configuration, the shape of the electrodes for forming contacts is of no importance per se for the functionality of sensors based on this technology. For example, the electrodes may be straight or in another kind of shape, provided that they form a contact with at least one nanowire at the base and at the top, and the one-dimensional nanostructure is the only electrically conductive connection between the electrodes. The circular electrodes are merely those that normally give the highest yield (highest yield of functioning sensors in the production operation).

The process presented here for production and alignment of nanowires only needs two micrometers of inexact optical lithography steps on the same substrate in order to produce a fully functioning electronic nanowire biosensor:
a) Lithography 1: localization of the gold catalysts on preferably circular micrometer-size areas
b) Growth of the nanowires, diameter 20-40 nm, length 10-20 micrometers
c) Alignment of the randomly 3D-oriented nanowires parallel to the substrate. The nanowires here typically lie radially outward, like the spokes of a wheel, proceeding from the hub.
d) Lithography 2: simultaneous deposition of preferably circular electrodes in the center of the "hub" and on the outside as a rim over the ends of the nanowires. The outer electrode has to have an orifice, by means of which the inner electrode can be contact-connected to a conductor track.

The number of contact-connected nanowires can be controlled in two ways:
a) Density of the catalyst particles in the original nucleation area defines the total number of nanowires.
b) The length of the nanowires has a standard Gaussian distribution. The distance of the outer electrode from the center can accordingly be matched to part of a length distribution. The other nanowires lie passive/redundant and are not contact-connected on the substrate.

Greatest industrial/economic advantage:

Inexpensive production.

No complex alignment techniques necessary; no costly electron beam lithography for the contact-connection of nanostructures.

Parallelizable for use on the wafer scale. Comparable components have been achievable to date only in individual complex laboratory prototypes. Or via nanoscale optical lithography, which requires extremely expensive and complex equipment.

For industrial parallel production of complete components by this method, the following are needed: a 25-year-old lithography system; an LPCVD oven; a metallization system.

Specifically, the present invention relates, in a first aspect, to a process for producing a conductive structure comprising at least one nanowire, especially a silicon nanowire, having a diameter of less than 50 nm, with which contacts are formed via at least two sites using electrodes, and wherein the at least one nanowire and the electrodes are arranged in one plane on a substrate. The process is more particularly characterized in that the following process steps are conducted:
a) catalytically active metal nanoparticles having a diameter in the range of 0.5-50 nm have been deposited on the surface of a preferably insulating substrate,
b) the surface and the metal nanoparticles deposited thereon are exposed to a gas stream comprising at least one gaseous nanowire-forming component, especially a silicon component, at a temperature in the range of 300-1100° C. over a period in the range of 10-200 min, forming at least one nanowire protruding from the substrate and having a length in the range of 5-200 μm (typically, lengths in the range of 10-100 μm, preferably in the range of 20-50 μm, are formed);

c) this at least one nanowire protruding from the surface of the substrate is laid down into a plane by placing a secondary substrate having a contact face corresponding to the surface of the insulating substrate on top;

d) contacts are formed either with the at least one nanowire laid down on the insulating substrate at two different sites with electrodes or with the at least one nanowire adhering on the secondary substrate at two different sites with electrodes.

The specified temperature range of 300-1400° C., preferably 300-1100° C., for the processing operation in step b) applies especially when the catalyst particles (metal nanoparticles) used are gold particles. If other materials, for example aluminum particles or titanium dioxide particles, are used, it may even be possible to use higher temperatures up to 1500° C. or even 2000° C. The growth temperature for various kinds of nanowires extends in principle from room temperature up to an upper limit which may even be well above 1000° C. Silicon nanowire growth at 1200° C. has been reported. For silicon, the highest possible temperature is close to the melting point, which is at 1410° C. For other materials, the upper temperature limit in the growth operation is similarly close to the respective melting point. The operating parameter windows may be correspondingly large. The operation works with such in principle with nanowires of the minimum length for which optical lithography is capable of assuring an exact alignment between the two lithography steps for a) catalyst deposition and b) electrode deposition. In other words, the minimum length of nanowires is restricted by the maximum alignment inaccuracy/tolerance between the two lithography steps. In modern equipment, the alignment tolerance of the lithography steps may be within a region of only a few hundred nanometers, and in some cases even below 100 nm. However, the economic advantage is that, by means of longer nanowires, even a low alignment tolerance in very inexpensive (and comparatively old) equipment enables reliable contact-connection of the nanowires via metal electrodes.

With regard to step c), the following should be added: the contact plane of the secondary substrate may be a flat plane or else a curved plane. In the case of a curved plane as the contact plane, the secondary substrate can, for example, roll over the surface of the primary substrate and thus bring the nanowires into a flat position. If the contact plane is a corresponding contact plane pressed onto the surface over the full area, it is essential that this contact plane of the secondary substrate corresponds to, i.e. is essentially complementary to, the surface of the primary substrate at this point, such that the structures are placed onto the plane of the primary substrate.

In addition, the alignment operation proposed for the nanowires is astonishingly suitable in principle for any one-dimensional nanostructure (nanowires composed of all available materials and likewise carbon nanotubes). This operating step c) should thus be viewed as an invention in its own right, i.e. not just for silicon nanowires having a diameter of less than 50 nm, with which contacts are formed via at least two sites using electrodes, and wherein the at least one nanowire and the electrodes are arranged in one plane on a substrate, not just for the process steps wherein catalytically active metal nanoparticles having a diameter in the range of 0.5-50 nm are deposited on the surface of a preferably insulating substrate, and wherein the surface and the metal nanoparticles deposited thereon are exposed to a gas stream comprising at least one gaseous silicon component at a temperature in the range of 300-1100° C. over a period in the range of 10-200 min, forming at least one nanowire protruding from the substrate and having a length in the range of 5-200 μm (typically, lengths in the range of 10-100 μm, preferably in the range of 20-50 μm, are formed).

In order to get the nanowires laterally and radially aligned on a substrate, the operation in which contacts are formed with the at least one nanowire deposited on the insulating substrate with electrodes at two different sites can be modified.

As described above, the nanowires are "pressed flat" on the growth substrate by an auxiliary. In this context, it is fundamentally a surprise that this is unexpectedly possible at all; the person skilled in the art would expect the nanowires in such an operation to be destroyed or else be made unusable. The first variant envisages contacting on the same substrate. Any anti-adhesive coating of the auxiliary can prevent the adhesion of nanowires on the auxiliary.

An improvement or a variant can be implemented not by immobilizing the nanowires on the growth substrate as described above but by applying them to a secondary substrate which is used rather than the auxiliary for pressing the nanowires flat. A specific adhesive coating on the secondary substrate, when the two substrates (primary growth substrate and adhesively coated secondary substrate) are pressed together, leads to transfer of the nanowires to the secondary substrate in lateral and radial alignment after separation of the two substrates. While the two substrates are being pressed together, the two substrates are prevented from coming into direct contact by the nanowires in between, as a result of which only the nanowires are in direct contact with the adhesive coating of the secondary substrate. An organic adhesive coating can be removed by means of plasma oxidation in a selective manner for the silicon after the transfer of the nanowires.

In a first preferred embodiment, the process proposed is characterized in that the insulating substrate is a substrate composed of silicon, silicon dioxide or glass. Possible further insulating substrates which can replace silicon oxide or glass with the same functionality are silicon nitride, etc. In principle, any electrically insulating substrate that withstands the respective operating temperatures is conceivable.

A further preferred embodiment is characterized in that the metal nanoparticles are gold nanoparticles, preferably having a diameter in the range of 5-50 nm, preferably in the range of 20-45 nm.

In a further preferred embodiment, the process is characterized in that, in the course of step a), the metal nanoparticles, in spatial terms, are deposited on the surface of the substrate in selectively bounded regions, typically using lithographic methods, for example by applying a layer of a photoresist, especially using optical lithography, preferably producing holes having a diameter in the range of 0.02-10 μm, preferably 0.5-5 μm, in this photoresist layer via selective exposure through a structured chromium mask (the holes extend down to the substrate), and by either subsequently applying a preferably aqueous solution carrying metal nanoparticles in colloidal form, preferably nanoparticles having a diameter in the range of 0.5-500 nm, especially preferably having a diameter in the range of 5-150 nm, to the photoresist, evaporating off the solution and subsequently removing the resist with a suitable solvent, preferably acetone, or by using electron beam metal vaporization under reduced pressure to apply a metal film, especially a gold film, to this photoresist layer, preferably having a layer thickness in the range of 0.1-2 nm, and by subsequently removing the photoresist and the metal present thereon by means of a suitable solvent, preferably acetone.

A further preferred embodiment of the process is characterized in that step b) is conducted at a temperature in the range of 350-500° C., preferably in the range of 400-480° C., especially preferably in the range of 450-470° C.

Yet a further preferred embodiment is characterized in that the gaseous silicon component used is a silane or a disilane, preferably in combination with a carrier gas, especially preferably nitrogen or hydrogen. It is possible with preference to use a gas flow rate in the range of 50-200 sccm of gaseous silicon component, especially of silane or disilane and a gas flow rate in the range of 100-300 sccm of carrier gas.

In general terms, it is found to be advantageous to work, in the course of step b), at a total pressure in the range of 1-50 mbar, preferably in the range of 2-10 mbar, over the substrate, is maintained.

A further preferred embodiment of the process proposed is characterized in that, in step a), the nanoparticles are deposited in at least one, preferably in more than one, mutually separate nucleation area, such that a multitude of nanowires is formed in step b) over each nucleation area, and in that preferably, in step d), a first central electrode is produced over the nucleation area, in contact with a first end of the nanowires, preferably by means of metal vapor deposition or photolithographic deposition, and a second electrode formed so as to at least partly surround the first electrode is produced, preferably by means of metal vapor deposition or photolithographic deposition.

Independently of the subject matter described above, namely of the process for production of a nanowire in the context of a circuit in one plane, the present invention additionally relates to a process for dry-chemical production of a depression in a crystalline substrate. This novel dry-chemical etching process enables structuring of crystalline substrates, especially monocrystalline substrates, very particularly monocrystalline silicon.

A locally positioned catalyst, especially a gold catalyst, enables the selective etching of silicon as a function of crystal orientation. The gold catalyst reduces the bond energy between silicon atoms in the <100> crystal plane. The silicon <111> surface is etched much more slowly than the silicon <100> surface. This allows etching of local, nanometer-size depressions into a silicon <100> surface, the sidewalls of which have the silicon <111> surface. This gives rise to pyramidal depressions of exactly geometrically defined proportions.

The depressions have exactly square to rectangular outlines, with right angles between the lateral edges on the substrate surface. The lowered flanks of the depressions have the silicon <111> orientation, the effect of which is that the four opposite/adjacent flanks of the depression meet at an atomically sharp point of intersection (inverted pyramids). The size of the depressions is dependent on the process duration and can therefore be controlled in a restricted manner without lithographic methods. The dimensions of the current structures which have also been confirmed experimentally are at an edge length of 0-400 nm with corresponding depth. What is novel about the process is particularly that a) there has been no dry-chemical selective etching process for silicon to date;
b) the etching process is locally limited by a catalyst, which replaces the use of lithography;
c) the dimensions of the structures can be controlled via the process parameters, specifically by the temperature and the duration in which the temperature is applied.

A similar etching mechanism is triggered by liquid potassium hydroxide solution, which has the same etching properties in terms of the orientation of the silicon crystal surfaces. However, this wet-chemical process requires complex lithography methods in order to locally limit the etching action of the liquid, in order, for example, to produce depressions with given dimensions.

Particular features are preferably possessed by the gold catalysts used, which are produced in a particular manner, and are only active if a certain maximum size (a few nanometers) is not exceeded. The operation typically proceeds at high temperatures, which lead to conversion of the catalytically dissolved silicon atoms to the gas phase.

A silicon wafer surface can be structured over a large area and homogeneously by this process, without the use of structure-limiting measures, for example in the form of etching barriers in the form of structured photoresists or metallic etching masks, since the etching action is locally limited by the catalyst and the positioning thereof on the substrate.

If this process is applied to correspondingly thin silicon layers having a thickness somewhat lower than the depth of the pyramids, orifices of a few nanometers in size, called nanopores, can be produced in a silicon membrane at the point of intersection of the side flanks, at the lowest point in the pyramids. These nanopores are currently a very important constituent in the development of nanopore-based biosensors which serve for electronic reading of DNA molecules; corresponding further aspects relating to sensors of this kind are described further down. For this purpose, a DNA molecule is conducted through such a nanopore and read electronically as it passes through the pore.

It is likewise possible to use such a process for surface magnification, which is an important operating step for enhancing the efficiency of solar cells.

Economic and technical advantages are found to include the following: very uncomplicated, robust and inexpensive structuring and production of nanostructures on whole wafers, entirely without the use of lithographic methods (self-assembly). Operational control of the dimensions allows a variety of variations without the purchasing of fragile, technically complex and hence costly lithography masks or the use of electron beam lithography. The production of exactly geometrically defined structures in the sub-50 nm range without any lithography measures allows the development of novel electronic components in parallelized form, on the wafer scale, which without this method would be producible only in the form of single prototypes in complex laboratory operations.

Independently of the subject matter described above, namely of the process for producing a nanowire in the context of a circuit in one plane, the present invention thus additionally relates specifically to a process for dry-chemical production of a depression in a crystalline substrate. This process is preferably characterized in that a catalyst particle is deposited on a surface of a crystalline substrate at the site for production of the depression, and in that, preferably in the presence of a gas atmosphere which prevents the oxidation of the substrate, at least the region at which the catalyst particle lies on the surface (preferably the entire substrate) is exposed to a temperature of at least 500° C., preferably of at least 750° C., especially preferably of at least 900° C., most preferably in the range of 900-1100° C., over a period of at least 5 min, preferably at least 15 min. This forms a funnel-shaped depression which extends into the volume of the substrate and has at least three delimiting faces which converge in the volume of the substrate in the manner of a funnel and which are formed by crystal planes of the crystalline substrate.

In this context, there is also a production variant for those nanopores composed of funnels in a thin membrane, a characteristic feature of which is that the funnels are specifically not deeper than the thickness of the membrane layer. The last couple of nanometers in a membrane layer which has not been completely etched through may be removed here from the reverse side (the reverse side of the exposed and undamaged membrane surface) by any kind of etching operation. This process has the advantage that it is thus possible to produce a single nanopore or an exactly defined number of nanopores in a large-area membrane, by stopping a sufficiently slow etching operation from the reverse side at the exact moment when the first (deepest) funnel orifice or an exactly defined number of funnel orifices has been opened by etching. This breakthrough (or the breakthroughs) can be detected, for example, by means of electrical or optical processes, and this enables the stopping of an etching operation at an exactly controlled/preferred number of nanofunnels opened at the tip.

In addition, the catalyst particle which at the end of the process is present in the depressions can be used as nucleation seed for a silicon nanowire growth, specifically in a process as described in the first aspect further up and in the first claims. This leads to a funnel-shaped structure with a nanowire attached at the lowest point; the present invention accordingly also relates to such a novel funnel-shaped structure in a silicon substrate.

A first preferred embodiment of this proposed process is characterized in that the crystalline substrate is a monocrystalline substrate, preferably composed of silicon, preferably a <100> silicon wafer (for example an SOI structure). When a monocrystalline <100> silicon substrate is used, a funnel with four converging delimiting faces is formed, which run from the surface and converge in the volume of the substrate and are formed by the <111> crystal planes of the single crystal. This is because it is found that the catalyst particle allows the depletion of the silicon along these planes to proceed much more slowly under the conditions mentioned, such that a funnel of this kind with exactly defined delimiting faces forms automatically.

Preferably, the surface of the substrate, especially of the silicon substrate, is treated beforehand in such a manner that an oxide layer thereon is removed.

A further preferred embodiment is characterized in that the catalyst particle is a metal nanoparticle, preferably a gold nanoparticle. In general, such a nanoparticle preferably has a mean diameter in the range of 1-20 nm, especially preferably 2-10 nm.

The nanoparticles can be deposited on the substrate in different ways. For example using a process as described above in connection with the production of a nanowire. In a further preferred embodiment, the procedure for the deposition of at least one gold nanoparticle, especially on silicon, is to produce a gold layer having a thickness in the range of 0.1-2 nm on the surface, preferably using an electron beam metal vaporization process, preferably under high vacuum, and to use this to form the gold nanoparticles on the basis of the different surface energies.

A further preferred embodiment of the process proposed is characterized in that the depression is a passage orifice through the substrate, which in this case to some degree takes the form of a plate having a defined layer thickness, by virtue of the thickness of the substrate being less than the geometric depth of the depression formed by the delimiting faces. In this case, the depression in the surface of the substrate typically has an exact inlet orifice formed by the lines of intersection between the surface and delimiting faces, and an outlet orifice formed by an opposite underside surface (or transition surface to a further, different layer, for example a layer of silicon dioxide) of the substrate and the delimiting faces, of smaller cross-sectional area, typically geometrically similar to the inlet orifice.

It is a characteristic feature of a further preferred embodiment that the inlet orifice has a rectangular or preferably square cross-sectional area having a side length of 50-500 nm, preferably in the range of 150-250 nm.

Further preferably, the depression preferably has a geometric depth formed by the delimiting faces in the range of 50-500 nm, especially preferably in the range of 150-250 nm, this geometric depth preferably being 1-50 nm, preferably 5-10 nm, greater than the thickness of the monocrystalline substrate, so as to form a passage orifice having an outlet orifice.

The present invention further relates, independently of the subject matter mentioned above, to a process for producing a sensor for measuring properties of long-chain molecules, to a correspondingly produced sensor and to a process for operating a sensor of this kind, especially for measuring the properties of DNA molecules or polypeptides or other polymers. In this context, the two processes described further up are preferably employed in the production operation.

The electrical resistance of a silicon nanowire or carbon nanotube is very sensitive to changes in the electrical charges or in the electrical fields at the surface of the 1-dimensional structure. Individual electronic charges or individual polarized molecules are sufficient to measurably alter the conductivity. By the elongation of a long-chain molecule (composed of different kinds of DNA/polypeptide constituents) at such a sensitive resistor, it is possible to read the signature of the individual molecular constituents by the change in resistance. This can be accomplished with or without prior biological functionalization of the sensor surface. It is likewise possible to use the piezoresistive properties of CNTs to detect binding forces. Through the combination of a 1-dimensional electrical conductor (CNT or nanowire), directly over a nanopore, it is possible to fix the molecule in position in the lateral direction through the nanopore. A different electrical potential on each side of the nanopore ensures that, for example, negatively charged DNA attempts to migrate through a nanopore. An opposing force at the opposite end of the molecule enables movement of the molecule back and forth through the pore at defined speed under mechanical stress. One end of the molecule (on the nanowire side) can be pulled through the pore by means of an AFM tip or magnetic bead/optical trap. This force is directed such that the mechanical stress deflects the molecule around the sensor (90°) in a similar manner to a winch, thus producing a fixed mechanical contact between molecule and sensor surface. The guiding through the nanopore ensures lateral stability and the production of the opposing force required to actively scan along the molecule in the stretched state and in mechanical contact with the 1D conductor at controlled speed.

The employment of nanopores is currently used to read passing DNA molecules. This is accomplished via the change of the ion current between two reservoirs which are separated from one another by a nanopore, while a DNA molecule passes through this pore. These nanopores are produced as individual pores in complex prototype work in TEM or by focused ion beam deposition. Problems with nanopore sensors include:
i) complex production of the nanopores
ii) inclusion of nanobubbles, which make use impossible and cause a lot of noise in the measurement
iii) it is very difficult to get the molecules through the pores of about 2 nm in size iv) production and operation is possible only under laboratory prototype conditions.

Nanowire and nanotube sensors have already been implemented per se, and have shown that very small binding forces/charge levels generate a measurable signal. Chemical and biological functionalization enables the selective binding of specific molecules and the perception thereof at the sensor. Currently, however, no long-chain molecule has yet been scanned along such a sensor, since it has not been technologically possible to date.

Advantages of the newly presented sensor element:
a) Nanobubbles are not a problem, since measurement is not effected within the pore. Nanobubbles probably do not occur since the pores can be greater than 2-10 nm in size.
b) Possible for the first time to analyze long-chain molecules with nanowire/nanotube sensors.
c) In combination with the two prior notices of invention, inexpensive parallel production of such sensors is possible with a low level of technical complexity.
d) Parallel operation of a plurality of sensors on one chip enables the parallel reading of many molecules, in order to accelerate the measurement rate, which is a critical factor in long-chain DNA molecules.
e) Very inexpensive production compared to components of similar complexity through use of rough-resolution, inexpensive optical lithography.

Specifically, the present invention relates correspondingly to a process for producing a sensor element, especially for determination of molecular properties of long-chain molecules such as, more particularly, DNA molecules or polypeptides, which is characterized in that the following process steps are run through, and the sequence can optionally also be altered:
a) in a substrate, especially in a monocrystalline silicon layer, a funnel-shaped passage orifice having a rectangular or square inlet orifice on a top side and an outlet orifice on a bottom side opposite the top side, which is smaller in terms of cross-sectional area, preferably at least five times smaller, especially preferably at least ten times smaller, is produced preferably using a process as described above;
b) in a region on the top side adjoining or close to the inlet orifice, either a nanowire is produced in a process as described above and is placed over the inlet orifice so as to form a bridge over it and contacts are formed on either side via electrodes, or a prefabricated CNT or nanowire is placed over the inlet orifice so as to form a bridge over it and contacts are formed on either side via electrodes;
c) the two electrodes are integrated into a circuit in which an electrical or electronic property can be measured using the CNT or nanowire, especially the resistance as a function of time, especially as a function of the position of a molecule being measured.

In a first preferred embodiment of such a process, this process is characterized in that, in the course of step a), proceeding from a silicone-based overall substrate having a surface monocrystalline <100> silicon layer having a thickness in the range of 5-500 nm, preferably in the range of 100-300 nm, a silicon dioxide layer beneath the latter and a silicon wafer beneath the latter, a funnel-shaped passage orifice in the silicon layer is produced in a dry-chemical or wet-chemical etching process, preferably in a process as per the above description, wherein a square or rectangular outlet orifice having a side length in the range of 2-10 nm is produced in the silicon layer on the side of the silicon dioxide layer, by removing the silicon wafer and the silicon dioxide layer in the region of this outlet orifice to expose the outlet orifice, by converting the silicon layer to an insulating oxidized silicon dioxide layer. Equally, as an alternative to the complete thermal oxidation of the silicon membrane, an insulating layer can be applied from the outside, either composed of silicon dioxide or another kind of electrically insulating material, which fully covers the surface of the silicon membrane but leaves the funnel tips/orifices open and free for passage.

It is a characteristic feature of a further preferred embodiment of this process that, in the region of the sensor element, either at the top side of the inlet orifice or at the bottom side of the outlet orifice, a region for receiving a liquid in which molecules to be measured can be kept is provided, and wherein means, especially in the form of magnetic and/or optical and/or electrooptical and/or mechanical moving elements, are additionally provided, with which a molecule which passes at least partly through the passage orifice can be moved through this passage orifice and past and around the nanowire, and wherein a circuit which enables establishment of a potential difference between the liquid region on the top side and the liquid region on the bottom side is especially preferably provided.

The present invention further relates to a sensor element, especially produced by a process as described above, which is characterized in that it includes an insulating substrate having a funnel-shaped passage orifice having a rectangular or square inlet orifice on a top side and an outlet orifice on a bottom side opposite the top side, which is smaller in terms of cross-sectional area, preferably at least five times smaller, especially preferably at least ten times smaller. After a thermal conversion process to silicon dioxide, the funnel orifice can optionally also be flattened out, and the end result may be a round orifice which no longer corresponds to the original square or rectangular cross section. A nanowire is arranged so as to engage with and form a bridge over the inlet orifice and is contact-connected on either side via electrodes, and these electrodes are or can be integrated into a circuit in which an electrical or electronic property can be measured by means of the nanowire, especially the resistance as a function of time, especially as a function of the position of a molecule being measured.

Preferably, a region for receiving a liquid in which molecules to be measured can be kept is provided either at the top side of the inlet orifice or at the bottom side of the inlet orifice.

Further preferably, means are additionally provided, especially in the form of magnetic and/or optical and/or electrooptical and/or mechanical moving elements, with which a molecule which passes at least partly through the passage orifice can be moved through this passage orifice and past and around the nanowire.

In addition, especially preferably, a circuit which enables establishment of a potential difference between the liquid region on the top side and the liquid region on the bottom side is provided.

The present invention further relates to a method for measuring properties of long-chain molecules, especially of DNA molecules or polypeptides, preferably using a sensor element as described above, which is characterized in that the molecule is coupled on one side to a resistance element, preferably in the form of a magnetic and/or optically addressable bead which is of such a size that it cannot pass through the passage orifice and which can be shifted by external influence in a three-dimensional manner relative to the passage orifice and laterally with respect to the surface, in that this molecule coupled to the resistance element is introduced into the liquid region on the top side, in that a potential difference between the top-side liquid region and the bottom-side liquid region is established, such that the free end of the molecule is pulled through the passage orifice and into the bottom-side liquid region, the resistance element remaining trapped in the top-side liquid region, and in that an external influence, especially in the form of a laser-single beam trap or in the form of a magnetic field, is applied, such that the resistance element is moved away from and/or closer to the passage orifice, optionally in an alternating operation, wherein the molecular chain is moved around the CNT or nanowire, forming contacts therewith, and in that an electrical or electronic property, preferably the change in resistance as a function of time, over the CNT or nanowire is measured.

Further embodiments are specified in the dependent claims.

BRIEF DESCRIPTION OF THE DRAWINGS

Preferred embodiments of the invention are described hereinafter with reference to drawings, which serve merely for elucidation and should not be interpreted in a limiting manner. The drawings show.

DESCRIPTION OF PREFERRED EMBODIMENTS

Figure 1:
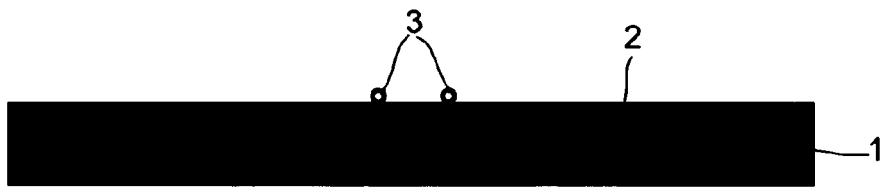
FIG. 1 the individual process steps for production of a nanowire in schematic view, showing in a) the substrate with nanoparticles deposited thereon, in b) nanowires grown thereon and protruding from the surface, in c) nanowires folded onto the surface using a secondary substrate, and in d1) the situation where the secondary substrate is designed exclusively for the folding-down of the nanowires and can be removed again, and in d2) that situation where the secondary substrate is adhesive and the nanowires remain stuck thereon.
Figure 1:
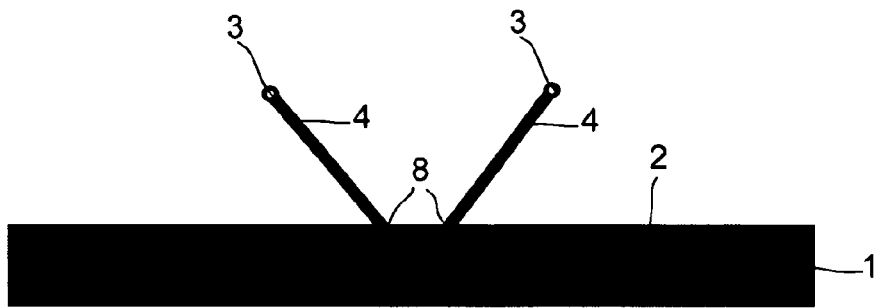
Figure 1:
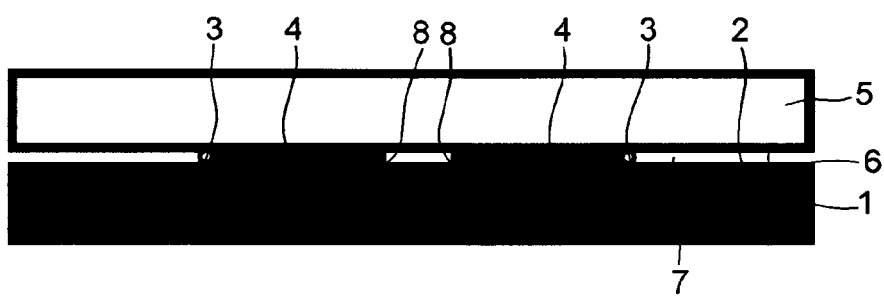
Figure 1:
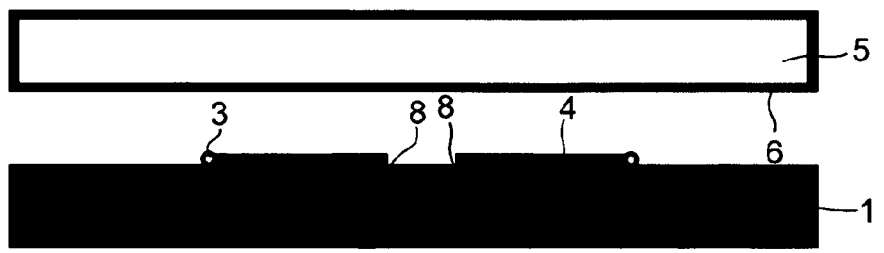
Figure 1:

In a first aspect of the present invention, this invention relates to a process for producing nanowire structures in an electrical circuit. This aspect is to be described in more detailed form hereinafter, namely in that processes for the production of large-scale arrays of electrical contacts with nanowires in lateral alignment on an insulating substrate are to be presented.

The process enables the efficient contact-connection of individual or of a limited number of nanowires with metal electrodes, for the purpose, for example, of producing biosensors in large-scale arrays, as already explained in the context of the third aspect and as will be detailed further down.

Background information relating to vapor-liquid-solid (VLS) nanowire growth operation:

Silicon nanowires can be grown locally by means of catalyst particles immobilized on a substrate. In a gas phase deposition operation, there is 1-dimensional fibrous crystal growth locally at the site of the catalyst particles. In the course of this, a silicon-containing gas is converted from the gas phase to a solid only at the site of the catalyst. The diameter of the crystal fibers is defined essentially by the diameter of the catalyst particles. Every catalyst particle produces a maximum of one crystal fiber (nanowire). Suitable catalyst particles for silicon are: gold, $TiO_2$, aluminum and further. For the various catalyst materials, there are different optimal operating temperatures. With gold, it is typically possible to grow nanowires between 325° C. and at most 1000° C. For other metals, higher minimum temperatures may apply.

The length of the crystal fibers is proportional to the process duration in an essentially linear manner.

Nanowires can be grown on any desired substrate that survives the chosen operating temperature unaffected. The operation chosen here proceeds at about 465° C. This is just below the temperature limit beyond which there is noncatalytic silicon deposition over the entire substrate.

Detailed process procedure (See Also FIG. 1):

Take a substrate 1, for example one with an electrically insulating surface 2, for example oxidized silicon or a glass substrate.

On this substrate 1, optionally after a cleaning operation, for example using the RCA standard cleaning method, a photoresist is applied by means of optical lithography, this comprising holes for the nanowire growth at the desired sites. For this purpose, the substrate is coated with a light-sensitive photoresist. This resist film is provided with the desired structures by selective exposure through a structured chromium mask present on a transparent quartz glass carrier. The operation is an operation for which many different resists with many different exposure parameters and layer thicknesses are suitable.

In the present case, they may be holes of diameter 0.02-10 micrometers. For many cases, 0.5-5 micrometers is suitable.

The holes in the resist at the desired sites then serve for selective deposition of gold catalyst particles at the sites where the substrate beneath is freely accessible.

There are two possible operations for this purpose, both of which the lead to identical/similar results:

a) An aqueous solution comprising gold nanoparticles (colloids) in the desired size is applied to the resist and the substrate. By means of pure physisorption, the gold colloids accumulate in the holes on the $SiO_2$ or glass substrate. The aqueous solution evaporates after a few hours, leaving the gold colloids immobilized on the surface. A suitable solvent (acetone) then removes the resist and the gold colloids immobilized thereon. All that remains is gold colloids at the sites on the substrate where the substrate was freely accessible through holes in the resist (called the lift-off process).

There are a wide variety of different sizes of gold nanoparticles in aqueous solution between 0.5 and 500 nanometers. In the course of experimental testing of the invention, 6-8 different solutions comprising particles of sizes between 5 nm and 150 nm in particular were tested: it was found that, surprisingly, only the gold colloids with diameter 40 nm are deposited in the holes on the substrate. For some, as yet unidentified reasons, none of the other sizes penetrate into the holes. As a result, it is possible to apply small gold colloids to the substrate in a structured manner via structuring by means of a photoresist and lift-off. The finding that about 40 nm particles are selectively deposited and work for this process is yet to be fully understood at present. Without being bound by this explanation, it appears at present to be the case that one physical reason for this could be that the gold colloids are subject to electrostatic interaction with the photoresist and do not penetrate into the holes for reasons of repulsion. The gold colloids of size about 40 nm, possibly as a result of the production, have a different surface chemistry/surface charge and therefore differ from the other particles. This could be a reason why the combination of optical lithography and aqueous solutions of gold colloids has found little attention to date for structured growth of silicon nanowires.

b) A second operation is likewise suitable for application of catalysts to the substrate via the pre-structuring of a photoresist. By means of electron beam metal vaporization (under reduced pressure), it is possible to apply a thin gold film to the structured resist layer and the substrate exposed in the holes. In the vapor deposition of gold layers having a nominal layer thickness of 0.1-2 nm, gold nanoparticles form on the substrate exposed in the holes. This process is already known per se; reference is made in this regard to Albuschies, J., M. Baus, O. Winkler, B. Hadam, B. Spangenberg, and H. Kurz, High-density silicon nanowire growth from self-assembled Au nanoparticles. Microelectronic Engineering, 2006. 83(4-9): p. 1530-1533; the more detailed description of the process given in this publication is accordingly incorporated into the present description.

The resist and the gold present thereon are removed from the substrate by means of a suitable solvent (for example, here specifically acetone). Only where the holes in the resist were do gold nanoparticles remain immobilized on the substrate beneath (lift-off process).

The gold particles 3 now applied in structured form (the resulting structure is shown schematically in FIG. 1a)) serve for local growth of silicon nanowires 4 on the substrate 1 (the situation after growth is shown schematically in FIG. 1b)).

The nanowires 4 have a diameter defined essentially by the individual catalyst particles 3. Since the substrate 1 beneath is amorphous, there is no given direction of growth (orientation) of the silicon crystal fibers in relation to the substrate.

In the region where the gold particles were present, after the growth process, there is a multitude of randomly oriented silicon nanowires which assume an angular distribution which has not been quantified exactly over the entire semicircular space above the substrate (like half a sea urchin lying on the substrate; see also FIGS. 2a) and b)).

The anchoring point 8 of the nanowires 4 on the substrate 1 is where the catalyst metal particle originally was. According to the length of nanowires 4, the nanowires 4 in lateral direction reach well beyond the point where the nanowires 4 are anchored on the substrate 1.

In order to be able to form electrical contacts between the nanowires 4 and metal electrodes 11/13, a lateral (parallel) alignment of the nanowires with respect to the substrate 1 is necessary.

For this process, the nanowires 4 must lie parallel on the electrically insulating substrate 1. It is essential for the process that the site and orientation of the nanowires 4 must be known in order to be able to apply metal electrodes 11/13 in a subsequent step. For this purpose, both ends of a nanowire 4 have to be connected between two different electrodes 11/13. The nanowires 4 are accordingly the only electrical connection between two macroscopic electrodes 11/13 that enables the incorporation of a single nanowire 4 or few nanowires 4 into a larger circuit.

Since the site of the catalyst particles is defined via optical lithography and is therefore known, it is merely necessary to determine the orientation.

Alignment markers can be applied to the substrate prior to the operation and define a coordinate system. Relative to this coordinate system, it is first possible to apply the catalyst particles, and these therefore define a site for the nanowires 4. When the orientation is known, it is then possible with the aid of the coordinate system on the substrate to apply the metal electrodes 11/13 for the respective nanowires 4 to the substrate 1.

The alignment operation in order to get the nanowires 4 parallel to the substrate 1 is based on the mechanical exertion of force on the nanowires 4 and the resulting permanent change in the direction of orientation of the nanowires 4, as shown schematically in FIGS. 1 c)-d).

An auxiliary 5 having a certain geometry is utilized in order to exert a force on the nanowires 4, such that the nanowires 4 not oriented parallel to the substrate 1, after the exertion of force, lie flat on the substrate 1, i.e. parallel to the surface 2 thereof.

For this purpose, any (vectorial) component of the force has to act at right angles, in the direction of substrate 1. This force can be exerted via a surface or curved surface of a secondary substrate 5.

In the case of a flat auxiliary, the nanowires are all pressed simultaneously onto the substrate (sandwich). In the case of a curved surface, the nanowires are pressed sequentially onto the substrate (as in the case of a rolling pin). A sphere which rolls over the substrate is likewise possible.

The nanowires 4, probably essentially because of van der Waals forces, remain immobilized on the substrate. A specific adhesive surface functionalization on substrate and nanowires can make the operation more efficient. For example, the use of an adhesive which does not adhere to the auxiliary but firmly bonds nanowires and substrate to one another can be used.

In order to prevent the nanowires from remaining stuck to the force-exerting auxiliary 5 (situation as per FIG. 1*d*1), a specific anti-adhesive coating can be provided on the auxiliary 5, which has fewer interactions with the nanowires 4 than the substrate 1 on which the nanowires 4 are to be immobilized. However, the operation in many cases works without adhesive or without anti-adhesive coating of the auxiliary 5.

Figure 2:
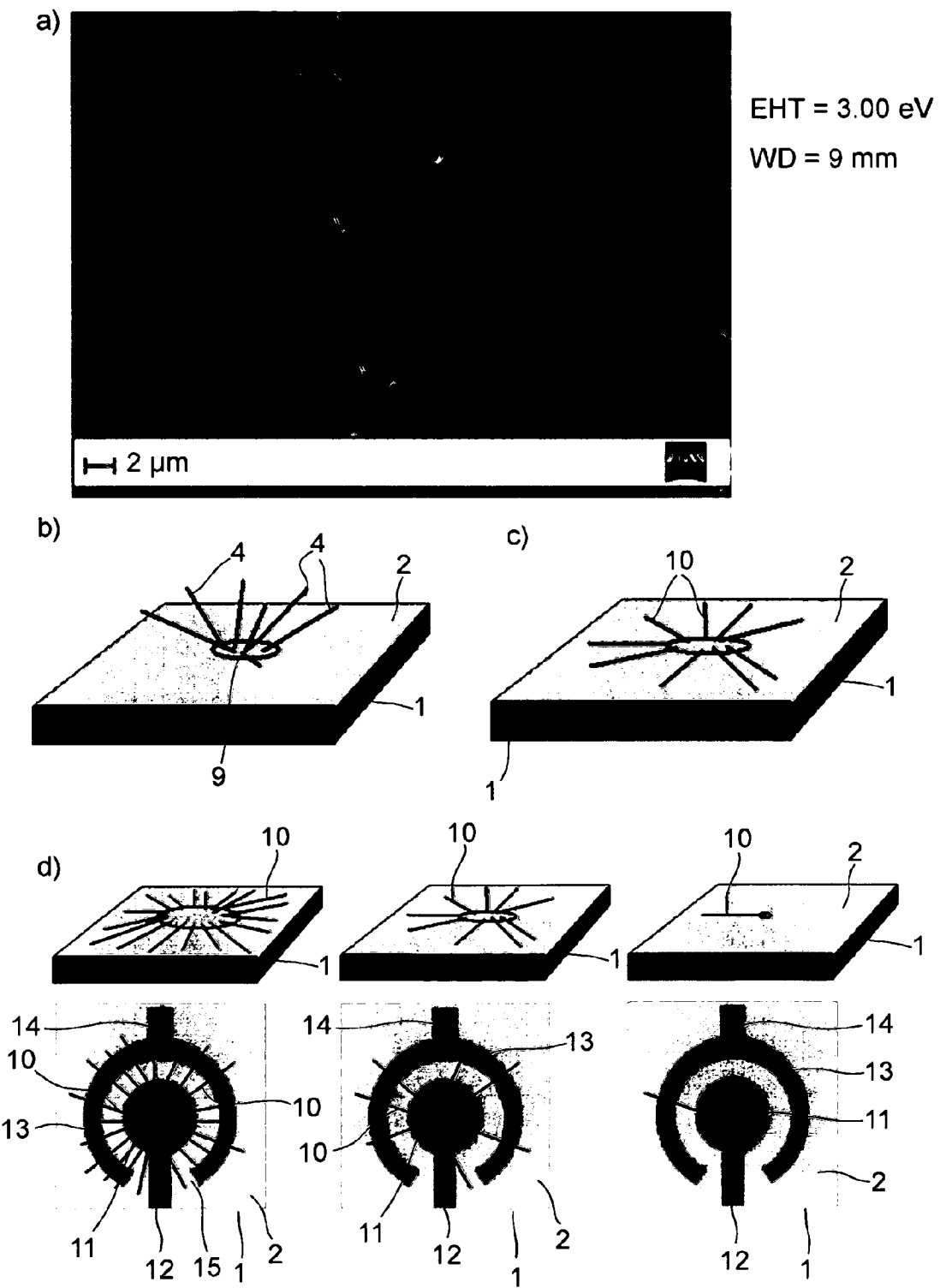
FIG. 2 in a) an electron micrograph of groups of nanowires on a substrate, in b) a schematic of a group of nanowires protruding from the plane in a nucleation area, in c) the group as per figure b) after the nanowires have been folded down, in d) various diagrams of nucleation areas with different numbers of nanowires, each from above in perspective views, beneath which are corresponding top views of nanowires contact-connected to electrodes for these different coverages.

When the diameter of the initial catalyst deposition area 9 is small in relation to the length of the nanowires, the nanowires after the alignment operation are oriented radially with respect to the site of the catalyst surface 2, as apparent, for example, from FIG. 2*c*).

With the knowledge of the radial arrangement and with the known center of the arrangement, precise application of the metal electrodes to the nanowires is possible, as illustrated in FIG. 2*d*).

The electrodes 11-14 can be produced via lithography and electron beam metal vaporization with subsequent lift-off operation.

In order to operate the arrangement in a liquid medium, a passivation/electrical insulation of the metal electrodes from the environment should typically also be undertaken, in order that the metal electrodes cannot be connected in an electrically conductive manner via the liquid medium.

Detailed description of the operation for production of the nanowires:

The gold catalysts (5-50 nm) are applied to a substrate 1 that withstands the operating temperatures of 465° C. chosen here. For the applications proposed, the substrates 1 may be silicon, silicon dioxide, or conventional glass.

The substrates 1 are introduced into an oven, which is normally used for gas phase deposition. In this case, this is an externally heated quartz glass tube in which the internal pressure can be controlled accurately.

At the operating temperature of 465° C., a gas mixture of silane and hydrogen is introduced into the process chamber. Disilane and other silicon-containing gases are is likewise possible ($SiH_4$ and $Si_2H_6$).

The pressure is reduced to 5 mbar during the operation. Since the silicon-containing gas is consumed during the operation, a continuous gas flow through the process chamber is ensured. The gas rates for the specific process are: 100 sccm (standard cubic centimeters) of silane and 200 sccm of hydrogen.

Hydrogen here is a carrier gas which does not have any direct chemical catalytic function and can be replaced by another gas, for example nitrogen. The operation also works with pure silane, or in the presence of other inert gases.

The process duration is typically 30-60 minutes, the process duration being directly proportional to the length of the resulting nanowires 4. The wires grow at a probably essentially constant growth rate over the process duration. With the given parameters, a growth rate of about 10-20 micrometers per hour is obtained. The diameter of the nanowires corresponds approximately to the size of the gold particles (5-50 nm). At the start of the process, there is a delay phase during which essentially no growth takes place. The growth sets in only after a few minutes (it is probable that there is initial activation and saturation of the catalyst particles, before the eutectic mixture of gold and silicon ideal for growth has formed).

The silane pressure (or partial pressure in the presence of other gases) and the temperature determine the growth rate. Higher pressure, and also higher temperatures, lead to faster growth.

What is important in this process is that no non-catalytic silicon deposition from the gas to the substrate takes place. Otherwise, the whole substrate (including between the catalyst particles) is coated with an amorphous silicon layer, and the electrically insulating properties, for example of an $SiO_2$ substrate, are adversely affected.

The non-catalytic deposition of silicon from silane gas commences at about 470° C. upward, and is relatively substrate-independent.

Typical parameters: substrate: $SiO_2$/glass; catalysts: gold nanoparticles (5-50 nm); operating temperature: 465° C.; process duration: 30-60 minutes; gas flow rate: 100 sccm of silane, 200 sccm of hydrogen; total pressure: 5 mbar.

As described above, the present invention additionally relates, in a further aspect, moreover, to a dry-chemical process for surface processing of monocrystalline substrates. This process is now to be described in detail with particular reference to FIG. 3, in the context of experimental details.

The process for the lithography-free production of pyramidal depressions in monocrystalline silicon with the aid of a novel dry-chemical etching process can be performed as follows:

The substrate 16 is a cleaned silicon wafer with the <100> crystal orientation in the substrate surface 18. The wafer should be oxide-free and is therefore freed of the natural oxide layer with hydrofluoric acid prior to the operation:

1 minute in an HF bath (hydrofluoric acid). Rinsing with deionized water (DI $H_2O$) for 10 minutes. However, the step for removing the natural oxide is not absolutely necessary. The natural oxide layer of about 2 nm in thickness is overcome during the operation by the etching action of the gold and does not constitute a definitively secure etching barrier between gold and silicon.

Thereafter, a gold layer is applied under high vacuum by means of electron beam metal vaporization. The nominal layer thickness is 0.1-2.0 nanometers.

The effect of the low nominal layer thickness is that not a continuous gold film but nanometer-sized gold (Au) clusters 17 are formed on the silicon surface 18 (cf. FIG. 3*a*). Other methods for applying Au nanoparticles 17 may also be suitable for the operation, for example operations as described above in the context of the first aspect of the invention.

The difference in surface energy between gold and silicon is responsible for the formation of Au nanoparticles 17. (On $SiO_2$, for example, the particles, for the same nominal layer thickness, will be about 2-5 times as large as on Si.)

The silicon wafer 16 with the gold particles 17 applied is heated at 950° C. under standard pressure in a tubular quartz oven under a nitrogen atmosphere or another inert gas (it is merely necessary to prevent oxidation of the silicon).

Figure 3:
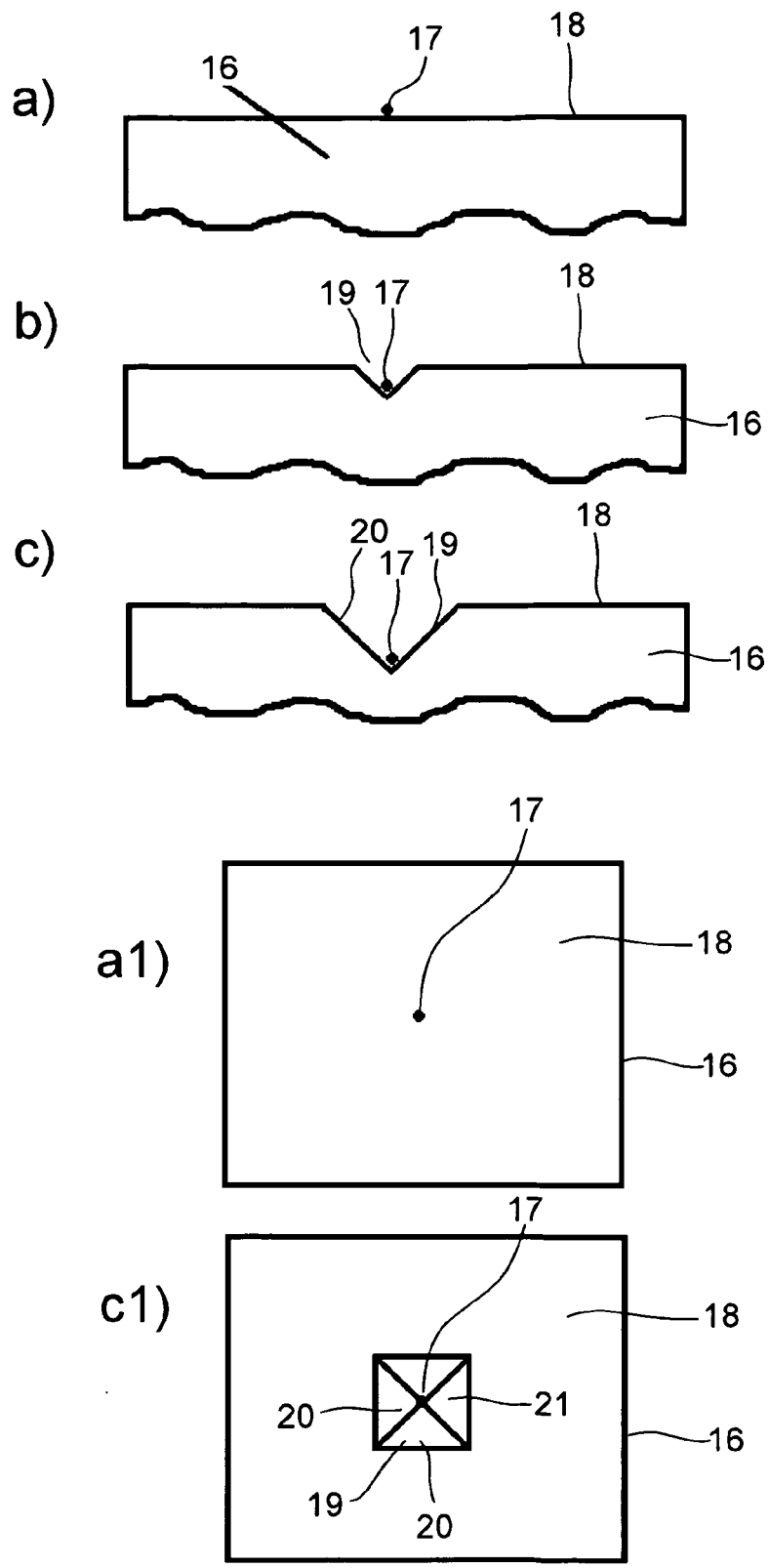
FIG. 3 the different process steps in the production of a funnel in a silicon substrate, wherein a) gives a schematic section diagram with gold particles lying thereon, a1) a top view of a), b) a diagram in a section after a first funnel growth, c) a diagram in a section after a deep funnel growth, and c1) a top view of the situation as per c)

At first, square depressions 19 of atomic size are formed, the dimensions of which grow proportionally over the operating time (cf. FIG. 3 *b*). The operating time defines the size/depth of the pyramidal depressions 19. After 30 minutes at 950°, the depressions have a diameter of about 200 nm. The depth corresponds to the flanks of the depressions descending at 57.x°, corresponding to the pyramidal form. The flanks 20 having the silicon <111> crystal surface meet (intersect) in the center of the depression 19 and form an atomically sharp fold.

Even though metal has been vapor-deposited homogeneously on the silicon surface, and the gold nanoparticles 17 have a very high density (number per unit area) as a result, the etched depressions form in a much smaller number per unit area.

Without any intention that restrictive character should be ascribed to such a theoretical explanation, it is suspected at present that the vapor deposition of the gold gives rise to a statistically distributed multitude of gold nanoparticles of different size, and that it is mainly a very particular size of the gold nanoparticles 17 that enables the catalytic etching of the silicon. The distribution of the etched depressions 19 in this case would correspond exactly to the distribution of the suitable gold particles 17 on the silicon surface. However, this is also explicable in that surface defects of the crystal structure in the silicon surface 18 act as nucleation seeds for the etching operation. In this case, the density of the pyramidal holes would be substrate-dependent and not particle-dependent.

For the further use of the nanostructured silicon surfaces, the excess gold can be removed by means of potassium iodide or other gold-dissolving operations (e.g. aqua regia).

In addition, the gold 17 in the depressions 20 can be used as a nucleation seed for silicon nanowire growth, specifically in a process as described within the first aspect further up and in the first claims. This gives silicon nanowires which grow out of the pyramidal holes.

Production of nanofunnels in a thin silicon membrane (in this regard, see also FIGS. 4 a)-c)):

Take a commercially available SOI wafer with the <100> crystal orientation as the silicon top layer: SOI=silicon on insulator.

An SOI wafer 23 is a conventional silicon wafer with normal thickness. However, on one side of the wafer is a thin silicon oxide layer 22 and above that a further thin monocrystalline silicon layer 21. In this arrangement, the oxide 22 is between the wafer 23 and the thin silicon layer 21.

Suitable dimensions for the layer thicknesses are: for the silicon top layer 21: 5-500 nm. The thickness of the oxide layer beneath is of minor importance. It preferably has to be thick enough to be able to stop the Au etching operation as an etching barrier (typically >5-10 nm).

The above-described dry-chemical etching operation is then executed on the SOI wafer. The dimensions, specifically the depth of the pyramidal depressions 19, are adjusted (over the process duration at 950°) such that the depth of the resulting holes/pyramids (the geometric pyramids defined from the delimiting faces) would be a non-zero number of nanometers deeper than the thickness of the top silicon layer. Example: 200 nm of silicon on insulator and pyramids of depth 205 nm. The result of this is that the etching operation is terminated at a depth of 200 nm at the oxide layer, forming pyramids with truncated tips.

At the base of the pyramids 19, at a depth of 200 nm, a plateau composed of the underlying $SiO_2$ layer 22 is formed.

The size of the plateau can be set very accurately. This is accomplished via the difference between nominal pyramid depth and thickness of the silicon top layer 21 present.

The SOI wafer can then be structured from the underside by means of conventional wet-chemical etching processes such that the underlying thick silicon layer and likewise the $SiO_2$ layer are removed (cf. diagrams in FIG. 4 b)-e) and corresponding, more detailed description further down). What remains is then only the original silicon top layer 21 as a free-floating membrane. Silicon is removed by means of potassium hydroxide solution, and the $SiO_2$ layer by means of hydrofluoric acid. For this purpose, the silicon top layer is protected by means of a potassium hydroxide- and HF-resistant protective film of a polymer material. Where the pyramidal depressions (at their lowest point) had the plateau of $SiO_2$, there are now correspondingly large orifices of the size of the plateau (pore/hole/aperture).

The Si 23 and the $SiO_2$ layer 22 on the underside of the SOI wafer can likewise be removed in a structured (local) manner, such that the majority of the wafer serves as a mechanical support for the free-floating thin silicon top layer 21. For this purpose, the underside of the wafer is structured by optical lithography. The orifices in the photoresist may be of a few micrometers to several millimeters in size, according to the requirement on the size/area of the free-floating thin silicon membrane provided with funnels.

As described above, the present invention also relates to a process for producing a sensor element, the latter preferably making use of the above-described processes for production of a nanowire or for production of a funnel-shaped hole in a silicon membrane. Alternatively, however, rather than a nanowire, it is possible to use, for example, a CNT, and the funnel-shaped orifice can also be produced in the silicon membrane using a wet-chemical process. The process for production is to be illustrated hereinafter with reference to FIG. 4 a)-k), and the mode of operation with reference to FIG. 4 l)-m).

Nanowire sensors with nanofunnels for analysis of long-chain molecules, sensor geometry and mode of operation (cf. FIG. 4):

The sensor consists of an electrically contact-connected silicon nanowire 4 or a carbon nanotube (CNT) present on an insulating substrate (an insulating membrane 18/29). Beneath the nanowire 4 (or CNT) is a nanofunnel 19, which constitutes an orifice on the underside of the substrate/membrane. The molecules 35 to be analyzed are long-chain polymers/polypeptides formed from different subunits (proteins/DNA). The electrical sensitivity of the nanowire 4 (CNT) allows detection of the individual subunits of the long-chain molecule 35 in direct physical contact between the two, and electronic measurement via the nanowire/CNT 4. For sequencing of all the subunits, the length of the molecule is pulled over the nanowire/CNT 4 and thus gives, in a sequential manner, the electrical information corresponding to the individual molecular units.

To improve the electrical detection of the molecular subunits, the nanowire/CNT 4 can be specially chemically functionalized in order to produce a stronger interaction between the individual subunits and the nanowire 4, which enhances the signals of the individual molecular units. In the case of DNA, the complementary base pairs can be applied to the nanowires/CNTs in order to generate a greater electrical signal through the binding.

There are two possible modes of operation in particular:

A) The interaction can be detected via the electrostatic and molecule-specific change in resistance of a nanowire/CNT (as in the case of detection of small molecules).

B) It is likewise possible to utilize the piezoresistive effect of a nanowire/CNT in order to identify the molecular units. The electrical resistance of a nanowire/CNT changes with any force exerted on the nanowire/CNT and the resulting expansion/change in length thereof. According to the functionalization of the nanowire/CNT, the molecular subunits bind with different strength to the nanowire/CNT and exert different forces on the nanowire/CNT in the sequential elongation, which can then be read electrically.

The specific geometry of the nanowire sensor with a funnel over a membrane allows exact positioning of the molecule over the nanowire and exertion of exactly directed tensile forces/pulling speeds for an accurately defined deflection of the molecule via the nanowire/CNT.

In order to be able to exert the directed forces on the molecule and to be able to position the molecule over the sensor, the molecules 35 are functionalized at one end with a polymer bead 36 of diameter 0.5-10 micrometers, such that it does not fit through the funnel 19. The polymer bead 36 likewise serves for movement of the individual molecules with the aid of an optical trap or, in the case of a magnetic bead, for movement thereof with a magnetic trap, and for positioning thereof via the funnel 19 (optical trap=focused light beam with which small objects can be moved in liquid). DNA can, for example, be chemically bound specifically to the respective ends with a wide variety of different objects/polymer beads.

The strong negative electrical charge 38 of DNA allows the molecule to be pulled through the funnel 19 to the underside, i.e. from the liquid region 33 into the liquid region 34 in the direction 39 shown schematically. This is accomplished by means of an electrical potential between the liquid regions 33/34 on the top and bottom sides of the membrane 29 in which the funnel orifice 19 is present. The electrostatic potential is generated via electrodes in the liquid, in each case above and below the insulating membrane 29. Without the polymer bead, the molecule 35 would be pulled through the funnel orifice.

The molecule then experiences an electrostatic pulling force 39 toward the bottom side: this force is aligned at right angles to the membrane. With the aid of an optical trap, it is then possible by means of the polymer bead 36 to exert a lateral pulling force on the molecule 35 counter to the electrostatic pulling force 39. As a result, the molecule 35 is put under strain and exerts a mechanical force on the nanowire as a result of the deflection thereby. In addition, because of the small dimensions of the exit orifice 27, the molecule is fixed exactly in its position relative to the wire 4. With the aid of the optical trap, it is possible to exactly control the pulling speed and to switch it back and forth reversibly in either direction. This enables multiple reading for reduction of measurement noise.

Optical instruments which can independently position and move up to one hundred optical traps on a substrate from a single laser source by means of acousto-optical beam dividers have now become available. As a result, it is possible to achieve a parallel mode of operation of a plurality of sensors on a substrate (parallel DNA sequencing).

Figure 4:
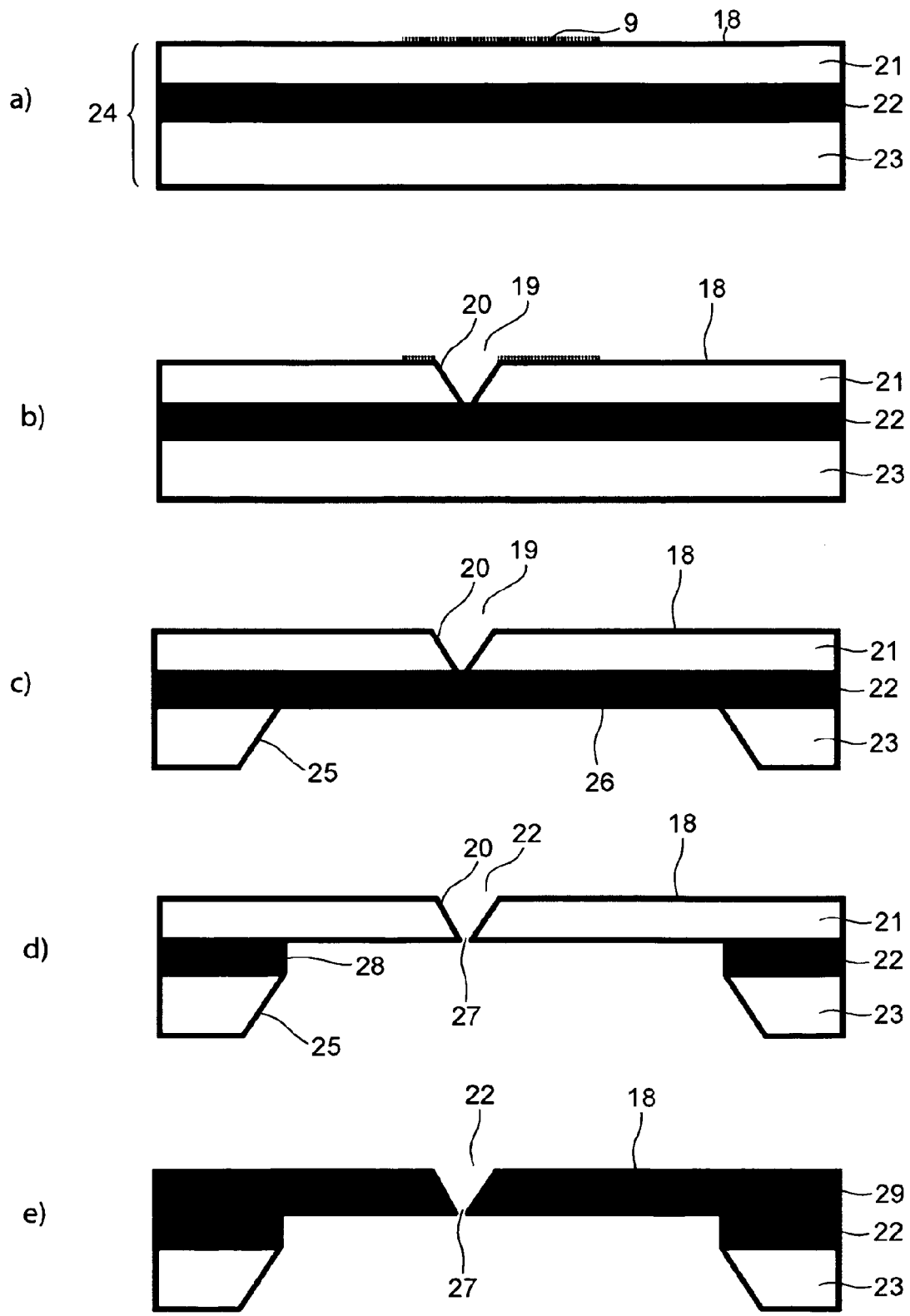
FIG. 4 the individual steps for the production of a sensor in their sequence in time and, in schematic section diagrams, the measurement principle, wherein a) shows an SOI substrate on which, by means of optical lithography, a defined area has been provided with a 0.5 nm vapor-deposited Au layer, b) shows the result of the Si etching operation run at 950° C., which produces nanofunnels distributed randomly in the above-defined area, c) shows the result of the steps of removal of the gold residues and the reverse-side etching of the Si wafer with KOH, where the top side for this process step should preferably be protected from the potassium hydroxide solution, for example by means of protective lacquer, d) the result of the removal of the $SiO_2$ layer by means of HF, e) the result of the conversion of the free-floating membrane in a thermal oxidation step to $SiO_2$ in order to give the desired electrical insulation, f) the result of the definition by means of optical lithography of the sites for the deposition of the gold catalyst particles, where the gold particles are deposited, g) the nanowires grown on the surface, where the gold particles locally catalyze the growth of Si nanowires and where the amorphous $SiO_2$ substrate causes the orientation to be random, h) the result of the lateral immobilization of the nanowires on the silicon oxide substrate with a non-adhesive auxiliary substrate, i) the contact-connection of the ends of the nanowires above the funnel, by means of optical lithography, with metal electrodes, j) coating of the metal electrodes by means of optical lithography with an insulating layer of $SiO_2$ or silicon nitride, k) a top view of the resulting sensor, where some of the metal electrodes remain free for integration into measurement electronics, and where the free portion of the metal electrodes is outside the liquid chamber in which the molecules to be examined are present, and where the nanowires are optionally chemically functionalized in order to enable controlled binding options with specific bases from DNA or other molecular units, l) a section diagram along the broken line in k) through a sensor, where the arrangement is embedded into a liquid chamber in which the DNA (or the like) molecules are present, and where the DNA has been functionalized with polymer beads or magnetic beads, where electrodes have additionally been immersed into the liquid chamber, in order to generate an electrostatic potential between the separated reservoirs, where the molecules are transported to the funnels via the appended beads by means of optical traps or a magnetic field, and where the electrostatic potential draws the DNA into the funnel and strains the molecule, and m) shows how, by means of optical traps or a magnetic field which is moved relative to the substrate (or vice versa), the molecules on the beads are pulled parallel to the substrate along the nanowires, with reading of the electronic signature via the nanowires.
Figure 4:
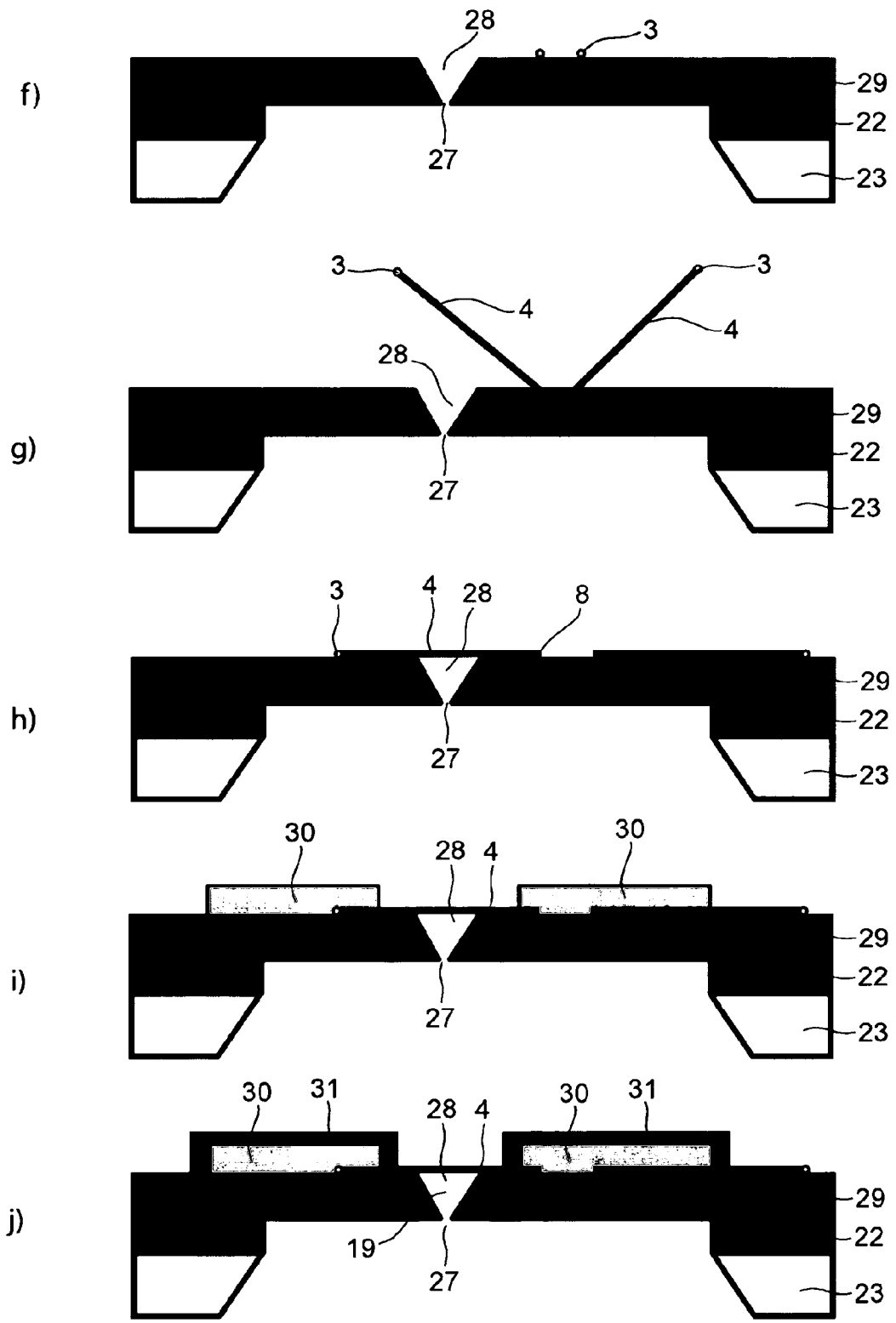
Figure 4:
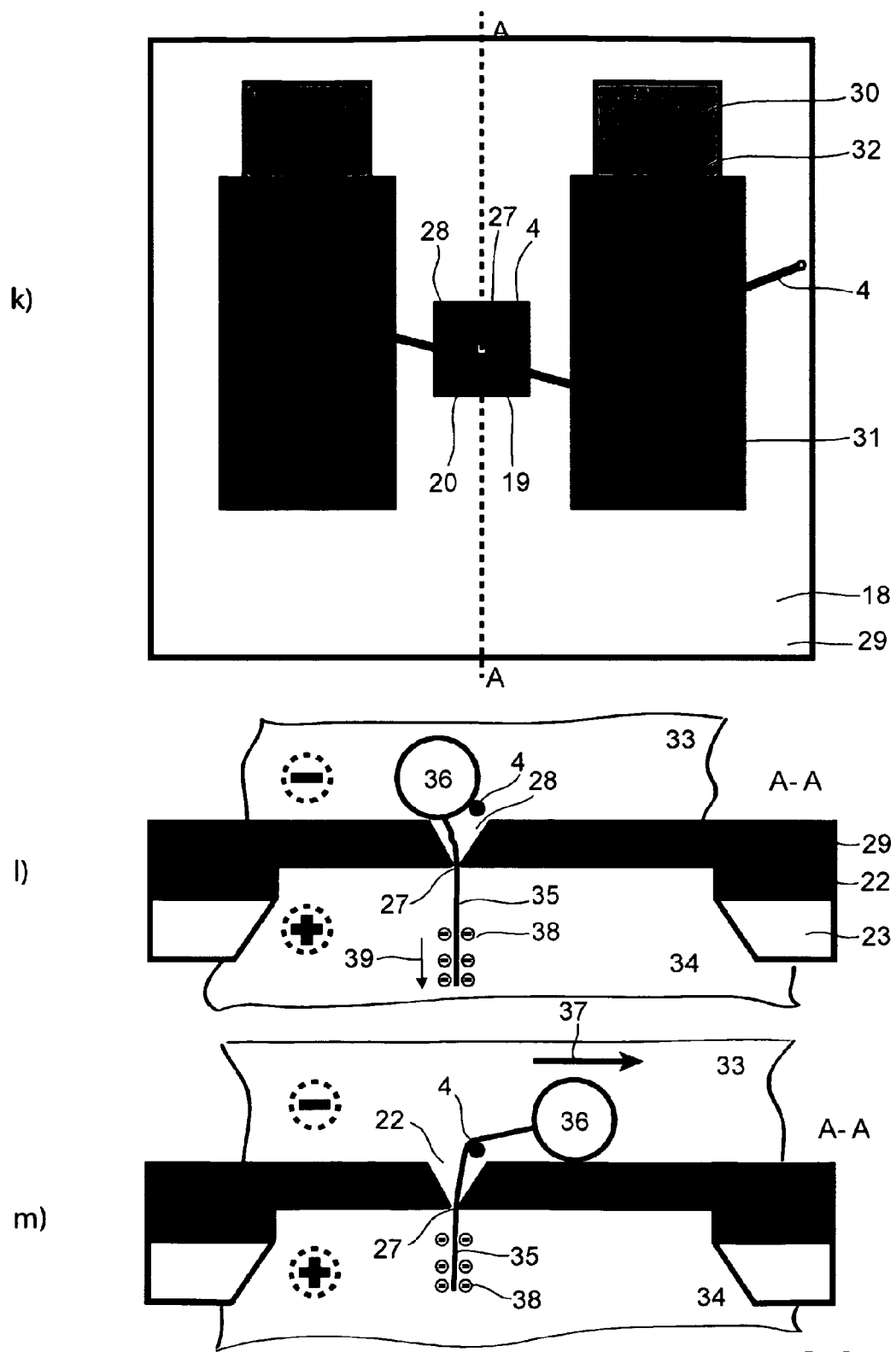

Production process (Cf. FIG. 4 a)-k) and corresponding description of figures):

Exactly as in the separate description already given above for the production of the nanofunnels in membranes, an SOI wafer 23/24 is taken.

By means of optical lithography, on the top silicon layer 21, the areas where the funnels 19 are to be present are defined. On these areas, the nominal layer thickness of 0.5 nm of gold is applied by vapor deposition, which leads to the layer 9 in clearly defined regions on the surface 18. The heating operation at 950° C. and the corresponding time gives the nanofunnels 19. As described separately, the silicon wafer is removed from the underside by means of potassium hydroxide solution and the $SiO_2$ layer is etched away by means of hydrofluoric acid. The now free-floating silicon membrane 21 is converted in a thermal oxidation step to electrically insulating $SiO_2$ to give the layer 29.

On the $SiO_2$ membrane 29 with the nanofunnels 19, by means of optical lithography, the areas where the gold catalyst particles 3 for growth of the nanowires 4 are to lie are defined at the desired sites. The areas for the nanowire growth are present directly alongside the areas where the nanofunnels 19 have been produced. The nanowire growth operation is executed as described separately.

Figure 5:
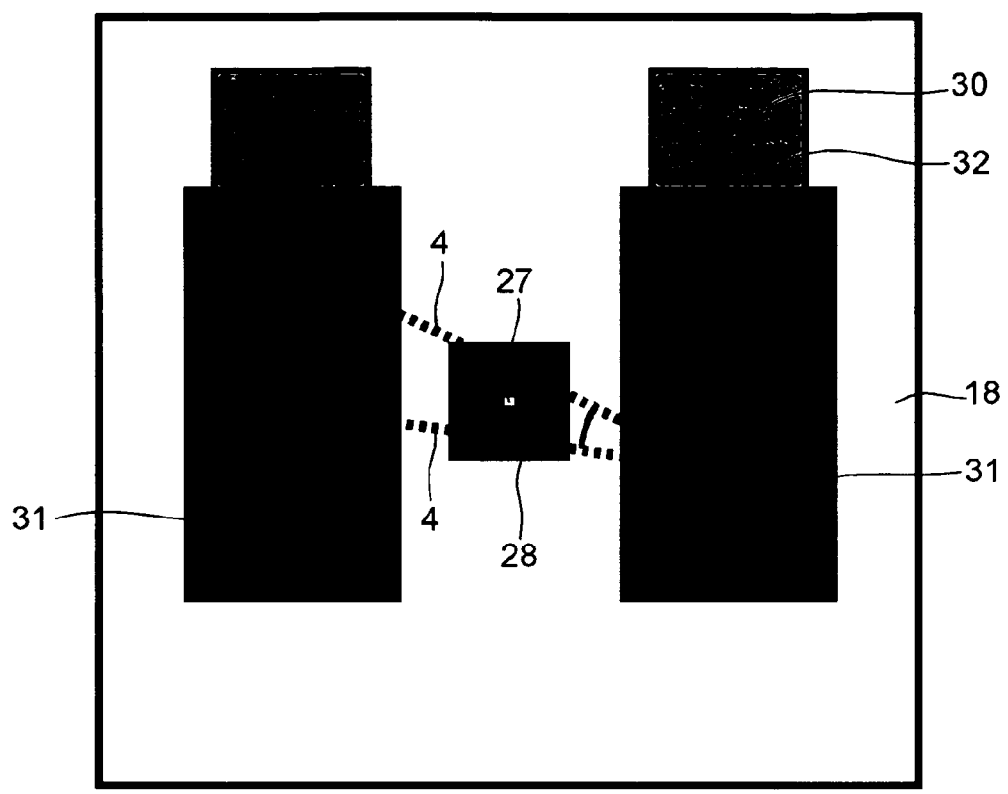
FIG. 5 in a top view, a diagram analogous to FIG. 4k), where nanowires in different distribution are shown over the same nanofunnel.

The unaligned nanowires 4 are immobilized laterally on the substrate 29 via the folding process. Some of the nanowires 4 will, as desired, be present over the nanofunnels 19, but a certain proportion will not. The distribution of well-positioned nanowires over funnels is random and can be varied up to a certain degree according to nanowire density and funnel density. This, however, is not a problem because the inlet orifice of the funnel is sufficiently large (see also FIG. 5). Through the large number of components 19/4 which can be produced in parallel on a substrate 29, even a relatively low yield of well-positioned nanowires 4 is sufficient to achieve a sufficiently large number of well-positioned nanowires 4 on a chip.

The laterally positioned nanowires 4 are then contact-connected via optical lithography with metal electrodes 30. In order to be able to operate the sensor arrangement in an electrolytic liquid 33/34, the metal electrodes 30 have to be electrically insulated from the environment. For this purpose, the metal electrodes 30 are coated with an electrically insulating layer 31 of $SiO_2$ or silicon nitride, leaving the nanowires 4 exposed (likewise by means of optical lithography).

To operate the sensor, the arrangement is embedded into a chamber suitable for microscopy, so as to form two separate liquid reservoirs 33/34 connected to one another only by the holes 19 in the membranes 29. In the separate reservoirs 33/34, there are additional electrodes in order to exert the electrostatic force on the DNA molecules and to pull them through the funnels 19.

By means of an optical microscope and optical traps, the beads 36 with the DNA 35 can be positioned over the suitable sensors, in order to pull the DNA 35 along the nanowires 4 and read it by electrical means.

| LIST OF REFERENCE NUMERALS | |
|---|---|
| 1 | Substrate, primary substrate |
| 2 | Substrate surface |
| 3 | Nanoparticle, gold particle |
| 4 | Nanowire |
| 5 | Secondary substrate, auxiliary |
| 6 | Surface of 5 |
| 7 | Gap |
| 8 | Attachment point of 4 to 2 |
| 9 | Region with nanoparticles, nucleation area |
| 10 | Flattened nanowires |
| 11 | Central electrode region |
| 12 | Connection of 11 |
| 13 | Partially surrounding second electrode |
| 14 | Connection of 13 |
| 15 | Cutout in 13 for 12 |
| 16 | Silicon substrate |

-continued

LIST OF REFERENCE NUMERALS

| | |
|---|---|
| 17 | Nanoparticle, gold particle |
| 18 | Surface of 16 |
| 19 | Recess, funnel in 16 |
| 20 | Delimiting face of 19, crystal plane |
| 21 | Silicon layer |
| 22 | Silicon oxide layer |
| 23 | Silicon wafer |
| 24 | Overall substrate |
| 25 | Underside recess in 23 after treatment with potassium hydroxide solution |
| 26 | Exposed surface of 22 |
| 27 | Outlet orifice of 19 |
| 28 | Inlet orifice of 19 |
| 29 | Oxidized layer 21, silicon oxide layer as insulating substrate layer |
| 30 | Metal electrode |
| 31 | Insulation layer |
| 32 | Contact region of 30 |
| 33 | Liquid on top side |
| 34 | Liquid on bottom side |
| 35 | Molecule strand |
| 36 | Bead, polymer bead |
| 37 | Lateral movement of 36 |
| 38 | Charges on 35 |
| 39 | Tensile force on 35 because of 38 and potential difference between 33 and 34 |
| 40 | Underside of 21/29 |

The invention claimed is:

1. A process for producing a sensor element for determination of molecular properties comprising:
   a) in a substrate a funnel-shaped passage orifice is generated having a rectangular or square inlet orifice on a top side and an outlet orifice on a bottom side opposite the top side, which is smaller in terms of cross-sectional area;
   b) in a region on the top side adjoining or close to the inlet orifice, either:
   1) a nanowire is produced having a diameter of less than 50 nm, with which contacts are formed via at least two sites with electrodes, wherein the at least one nanowire and the electrodes are arranged in one plane on a substrate, wherein
      a1) catalytically active metal nanoparticles having a diameter in the range of 0.5-50 nm are deposited on the surface of an insulating substrate;
      b1) the surface and the metal nanoparticles deposited thereon are exposed to a gas stream comprising at least one gaseous silicon component at a temperature in the range of 300-1100° C. over a period in the range of 10-200 minutes, forming at least one nanowire protruding from the substrate and having a length in the range of 5-200 µm;
      c1) this at least one nanowire protruding from the surface of the substrate is laid down into a plane by placing a secondary substrate having a contact face corresponding to the surface of the insulating substrate on top; and
      d1) contacts are formed either with the at least one nanowire laid down on the insulating substrate at two different sites with electrodes or with the at least one nanowire adhering on the secondary substrate at two different sites with electrodes and is placed over the inlet orifice so as to form a bridge over it and contacts are formed on either side via electrodes, or
   2) a prefabricated carbon nanotube (CNT) or nanowire is placed over the inlet orifice so as to form a bridge over it and contacts are formed on either side via electrodes; and
   c) the two electrodes are integrated into a circuit in which an electrical or electronic property can be measured using the CNT or nanowire.

2. The process according to claim 1, wherein the substrate in step a) is a monocrystalline silicon layer.

3. The process according to claim 1, wherein the rectangular or square inlet orifice on the top side is at least five times smaller in terms of cross-sectional area than the outlet orifice on the bottom side opposite the top side.

4. The process according to claim 1, wherein the rectangular or square inlet orifice on the top side is at least ten times smaller in terms of cross-sectional area than the outlet orifice on the bottom side opposite the top side.

5. The process according to claim 1, wherein the electrical or electronic property measured in step c) using the CNT or nanowire, is the resistance as a function of time and/or as a function of the position of a molecule being measured.

6. The process according to claim 1, wherein, in the course of step a), proceeding from a silicone-based overall substrate having a surface monocrystalline <100> silicon layer having a thickness in the range of 5-500 nm, a silicon dioxide layer beneath the latter and a silicon wafer beneath the latter, a funnel-shaped passage orifice in the silicon layer is produced in a dry-chemical or wet-chemical etching process, wherein a square or rectangular outlet orifice having a side length in the range of 2-10 nm is produced in the silicon layer on the side of the silicon dioxide layer, by removing the silicon wafer and the silicon dioxide layer in the region of this outlet orifice to expose the outlet orifice, by converting the silicon layer to an insulating oxidized silicon dioxide layer.

7. The process according to claim 1, wherein, in the course of step a), proceeding from a silicone-based overall substrate having a surface monocrystalline <100> silicon layer having a thickness in the range of 100-300 nm, a silicon dioxide layer beneath the latter and a silicon wafer beneath the latter, a funnel-shaped passage orifice in the silicon layer is produced in a dry-chemical or wet-chemical etching process, wherein a square or rectangular outlet orifice having a side length in the range of 2-10 nm is produced in the silicon layer on the side of the silicon dioxide layer, by removing the silicon wafer and the silicon dioxide layer in the region of this outlet orifice to expose the outlet orifice, by converting the silicon layer to an insulating oxidized silicon dioxide layer.

8. The process according to claim 1, wherein, in the region of the sensor element, either at the top side of the inlet orifice or at the bottom side of the outlet orifice, a region for receiving a liquid in which molecules to be measured can be kept is provided, and wherein magnetic, optical, electro optical, mechanical moving elements, or combinations thereof, are additionally provided, with which a molecule which passes at least partly through the passage orifice can be moved through this passage orifice and past and around the nanowire.

9. The process according to claim 1, wherein, in the region of the sensor element, either at the top side of the inlet orifice or at the bottom side of the outlet orifice, a region for receiving a liquid in which molecules to be measured can be kept is provided, and wherein magnetic, optical, electro optical, mechanical moving elements, or combinations thereof, are additionally provided, with which a molecule which passes at least partly through the passage orifice can be moved through this passage orifice and past and around the nanowire, and wherein a circuit which enables establishment of a potential difference between the liquid region on the top side and the liquid region on the bottom side is provided.

10. The process according to claim 1, wherein the insulating substrate in the production of the nanowire in step b) is a substrate composed of silicon, silicon dioxide, silicon nitride, or glass, and wherein the metal nanoparticles are gold nanoparticles.

11. The process according to claim 10, wherein the metal nanoparticles have a diameter in the range of 5-50 nm.

12. The process according to claim 10, wherein the metal nanoparticles have a diameter in the range of 20-45 nm.

13. The process according to claim 1, wherein, in the course of step a1), the metal nanoparticles are deposited on the substrate in spatially restricted and mutually separated regions, and by
   either subsequently applying a solution carrying metal nanoparticles in colloidal form,
   or by using electron beam metal vaporization under reduced pressure to apply a metal film to this photoresist layer, and by subsequently removing the photoresist and the metal present thereon by means of a suitable solvent.

14. The process according to claim 1, wherein, in the course of step a1), the metal nanoparticles are deposited on the substrate in spatially restricted and mutually separated regions by applying a layer of a photoresist, using optical lithography producing holes having a diameter in the range of 0.02-10 μm, or 0.5-5 μm in this photoresist layer via selective exposure through a structured chromium mask, and by either:
   subsequently applying an aqueous solution carrying metal nanoparticles in colloidal form, nanoparticles having a diameter in the range of 0.5-500 nm or having a diameter in the range of 5-150 nm, to the photoresist, evaporating off the solution and subsequently removing the resist with a suitable solvent,
   or by
   using electron beam metal vaporization under reduced pressure to apply to this photoresist layer a gold film having a layer thickness in the range of 0.1-2 nm, and by subsequently removing the photoresist and the metal present thereon by means of a suitable solvent.

15. The process according to claim 1, wherein step b1) is conducted at a temperature in the range of 350-500° C., and by using a silane or a disilane as the gaseous silicon component, and by maintaining a total pressure in the range of 1-50 mbar over the substrate.

16. The process according to claim 1, wherein step b1) is conducted at a temperature in the range of 450-470° C., and by using a silane or a disilane as the gaseous silicon component in combination with a carrier gas, nitrogen or hydrogen, using a gas flow rate in the range of 50-200 sccm of silane or disilane and a gas flow rate in the range of 100-300 sccm of carrier gas, and by maintaining a total pressure in the range of 2-10 mbar, over the substrate.

17. The process according to claim 1, wherein, in step a1), the nanoparticles are deposited in at least one, or in more than one, mutually separate nucleation area, such that a multitude of nanowires is formed in step b) over each nucleation area, and, in step d), a first central electrode is produced over the nucleation area, in contact with a first end of the nanowires, by means of metal vapor deposition or photolithographic deposition, and a second electrode formed so as to at least partly surround the first electrode is produced, by means of metal vapor deposition or photolithographic deposition.

18. The process according to claim 1, wherein for step a) a process for dry-chemical production of a depression in a crystalline substrate is used, wherein
   a catalyst particle is deposited on a surface of a crystalline substrate at the site for production of the depression, and wherein, in the presence of a gas atmosphere which prevents the oxidation of the substrate, at least the region at which the catalyst particle lies on the surface is exposed to a temperature in the range of 900-1100° C., over a period of at least 15 minutes, forming a funnel-shaped depression which has at least three delimiting faces, which converge in the volume of the substrate, and which are by crystal planes of the crystalline substrate.

19. The process according to claim 18, wherein the crystalline substrate is a monocrystalline substrate composed of silicon.

20. The process according to claim 18, wherein the crystalline substrate is an SOI structure, the delimiting faces thereof being four (111) crystal planes of the single crystal which run from the surface and converge in the volume of the substrate.

21. The process according to claim 1, wherein the catalyst particle is a gold nanoparticle having a diameter in the range of 1-20 nm.

22. The process according to claim 1, wherein the catalyst particle is a gold nanoparticle having a diameter in the range of 2-10 nm, the gold nanoparticles being produced on the surface by producing a gold layer having a thickness in the range of 0.1-2 nm on the surface using an electron beam metal vaporization process under high vacuum, and using this to form the gold nanoparticles on the basis of the different surface energies.

23. The process according to claim 1, wherein the depression is a passage orifice through the substrate, by virtue of the thickness of the substrate being less than the geometric depth of the depression formed by the delimiting faces, and the depression in the surface of the substrate having an inlet orifice formed by the lines of intersection between the surface and delimiting faces, and an outlet orifice formed by an opposite underside surface of the substrate and the delimiting faces of smaller cross-sectional area geometrically similar to the inlet orifice.

24. The process according to claim 23, wherein the inlet orifice has a polygonal, rectangular, or square cross-sectional area having a side length of 50-500 nm.

25. The process according to claim 23, wherein the inlet orifice has a polygonal, rectangular, or square cross-sectional area having a side length of 150-250 nm, and wherein the depressions have a geometric depth formed by the delimiting faces in the range of 150-250 nm.

26. The process according to claim 23, wherein the geometric depth is 1-50 nm, or 5-10 nm, greater than the thickness of the substrate, so as to form a passage orifice having an outlet orifice.

27. The sensor element, produced by the process claimed in claim 1,
   wherein the sensor element includes an insulating substrate having a funnel-shaped passage orifice having an inlet orifice on a top side and a smaller outlet orifice on a bottom side opposite the top side, which is smaller in terms of cross-sectional area,
   wherein a nanowire or CNT is arranged so as to engage with and form a bridge over the inlet orifice and is contact-connected on either side via electrodes, and these electrodes are or can be integrated into a circuit in which an electrical or electronic property can be measured by means of the nanowire or CNT.

28. A method for measuring properties of long-chain molecules, such as DNA molecules, using the sensor element as claimed in claim 27, wherein the molecule is coupled on one side to a resistance element,
wherein this molecule coupled to the resistance element is introduced into the liquid region on the top side,
wherein a potential difference between the top-side liquid region and the bottom-side liquid region is established, such that the free end of the molecule is pulled through the passage orifice and into the bottom-side liquid region, the resistance element remaining trapped in the top-side liquid region, and
wherein an external influence is applied, such that the resistance element is moved away from and/or closer to the passage orifice, optionally in an alternating operation, wherein the molecular chain is moved around the CNT or nanowire, forming contacts therewith, and
wherein an electrical or electronic property, such as the change in resistance as a function of time, over the CNT or nanowire is measured.

29. A method for measuring properties of long-chain molecules, such as of DNA molecules, using a sensor element as claimed in claim 27, wherein the molecule is coupled on one side to a resistance element in the form of a magnetic and/or optically addressable bead which is of such a size that it cannot pass through the passage orifice and which can be shifted by external influence in a three-dimensional manner relative to the passage orifice and laterally with respect to the surface,
wherein this molecule coupled to the resistance element is introduced into the liquid region on the top side,
wherein a potential difference between the top-side liquid region and the bottom-side liquid region is established, such that the free end of the molecule is pulled through the passage orifice and into the bottom-side liquid region, the resistance element remaining trapped in the top-side liquid region, and
wherein an external influence, in the form of a laser-single beam trap or in the form of a magnetic field, is applied, such that the resistance element is moved away from and/or closer to the passage orifice, optionally in an alternating operation, wherein the molecular chain is moved around the CNT or nanowire, forming contacts therewith, and wherein an electrical or electronic property, namely, the change in resistance as a function of time, over the CNT or nanowire is measured.

* * * * *